(12) United States Patent
Tang

(10) Patent No.: US 11,219,660 B2
(45) Date of Patent: Jan. 11, 2022

(54) ACID-RELIEF AGENT AND METHOD OF PREPARATION

(71) Applicant: Tieh-Chun Tang, West Covina, CA (US)

(72) Inventor: Tieh-Chun Tang, West Covina, CA (US)

( * ) Notice: Subject to any disclaimer, the term of this patent is extended or adjusted under 35 U.S.C. 154(b) by 152 days.

(21) Appl. No.: 15/998,364

(22) Filed: Aug. 10, 2018

(65) Prior Publication Data

US 2019/0374594 A1    Dec. 12, 2019

(51) Int. Cl.

| A61K 36/87 | (2006.01) |
|---|---|
| A61K 36/00 | (2006.01) |
| A61K 36/39 | (2006.01) |
| A61P 1/04 | (2006.01) |
| A61K 33/06 | (2006.01) |
| A61K 33/10 | (2006.01) |
| A61K 36/02 | (2006.01) |
| A61K 36/185 | (2006.01) |
| A61K 36/48 | (2006.01) |
| A61K 36/60 | (2006.01) |
| A61K 36/81 | (2006.01) |

(52) U.S. Cl.
CPC ............... *A61K 36/87* (2013.01); *A61K 33/06* (2013.01); *A61K 33/10* (2013.01); *A61K 36/02* (2013.01); *A61K 36/185* (2013.01); *A61K 36/39* (2013.01); *A61K 36/48* (2013.01); *A61K 36/60* (2013.01); *A61K 36/81* (2013.01); *A61P 1/04* (2018.01)

(58) Field of Classification Search
None
See application file for complete search history.

(56) References Cited

U.S. PATENT DOCUMENTS

| 9,902,956 B2 * | 2/2018 | Maor ................. C12N 15/8271 |
| 2005/0136169 A1 * | 6/2005 | Haung ..................... A23L 2/68 |
| | | 426/590 |

* cited by examiner

*Primary Examiner* — Michael Barker
*Assistant Examiner* — Randall O Winston
(74) *Attorney, Agent, or Firm* — Gary C. Honeycutt

(57) ABSTRACT

An acid-relief agent comprising a fermented vegetable extract obtained from a mixture of banana leaves, sweet potato roots, potato skin, seaweed, grape leaves, tendrils leaves, fig roots, emperor bean roots, and deep sea water; and nanocalcium mineral powder obtained from the thermal decomposition and grinding of a mixture of mica ore, mother of pearl, oyster shells. and oyster bay.

4 Claims, No Drawings

ACID-RELIEF AGENT AND METHOD OF PREPARATION

FIELD OF INVENTION

The present invention relates to the technical field of acid neutralizers, and in particular to a sustained relief agent rich in sodium ion, potassium ion and nanocalcium, and its method of preparation.

BACKGROUND

At present, environmental pollution and food safety are the major livelihood topics that people are concerned about. The heavy use of contaminated air, electron radiation, and various additives in foods can cause imbalances in chemical composition and acidity in the human body. Acidic compounds are used as food additives, detergents, bactericides, and disinfectants in our daily lives. These acidic chemicals can harm humans and cause secondary pollution, especially in food, drinking water, and beverages. It is easy to ingest into the body through the oral cavity, and at the same time, the cleaning agent used by people can easily enter the body through the skin.

Common in foods such as: fruit, vegetables, meat, poultry and seafood are frequent use of chemical fertilizers, pesticides, antibiotics and growth hormones, and all kinds of food additives, these items can promote the plant growth and used to keep the beautiful appearance, all of the remaining on the surface or internal acid compounds, especially the human daily intake of food surface accumulation of harmful chemicals, which makes human body more and more acidic. Cleaning products, such as, 90% of the soap, shampoo containing sodium dodecyl sulfate (SDS), lauryl sulfate (SLES), laurel composition of pure poly (ether sodium sulfate (SLS), one drop of the solution will remain in the body for 5 days, these soaps and shampoos are very strong, and the acid compounds are gradually make damage to our skin. In terms of food and drug safety, substances with an acidity below standard should be strictly controlled. Therefore, how to balance human pH has become a research trend nowadays, and the demand for health products has also increased sharply. The purpose of this present invention is to provide a rich in sodium potassium ions and nano calcium in order to meet the shortcomings of the existing technology.

The preparation of relief agent can thoroughly remove ingredients and ingredient within the surface of the harmful pesticides, pesticides, antibiotics and growth hormones and other acidic compounds and heavy metals, its ingredients are all natural, and the preparation technology is simple, stable control.

SUMMARY OF THE INVENTION

A method for preparing an acid-relief agent including sodium and otassium ions, plus nanocalcium and plant extracts, including the following steps:
a) fermenting a mixture of banana leaves, sweet potato rhizome, potato skin, seaweed, grape leaves, tendrils leaves, figs rhizome, and emperor bean rhizome.
b) mixing the fernented mixture with deep seawater and filtering to recover a vegetable extract rich in potassium and sodium ions.
c) mixing the vegetable extract with nanocalcium mineral powder.
d) adding and stirring deep seawater to the mixture of step c
e) granulating the mixture of step d) to recover the final product.

DETAILED DESCRIPTION

Step a) the Preparation of Natural Plant Extracts
a1) Take plant mixture rich in sodium potassium, by the percentage of volume, to add *lactobacillus* bacteria liquid 0.02~0.06%, lactic *streptococcus* bacteria liquid 0.01~0.05% and 0.01 0.04% of acetic acid *bacillus* bacteria liquid and *Kluyveromyces marxianus* 0.02~0.06%, after blending, stacking fermentation under 30~50° C. 15~30 days, then fermentation plant mixture is formed.

The plant mixture comprises more than two mixtures they are banana leaves, sweet potato rhizome, potato skin, seaweed, grape leaves, tendrils leaves and figs rhizome, emperor bean rhizome.

a2) extract the fermented plant mixture and mix with the deep seawater by weight ratio 1:(8~10) 2~3 times and combine the filtrate to obtain the natural plant extracts rich in sodium and potassium ions;

Step b) Prepare Mineral Powder Rich in Nano Calcium
b1) prepared by the weight ratio take 30-50 portion of Mica Ore, the mother of pearl 8-15 portion, 10-15 portion of oyster shells and oyster bay 22-28 portion. Using high pressure blast cleaning to remove dirt on the surface of the raw material;
b2) grind the cleaned mixed material into 250-350 particles in which the mixture will be frozen and dried.
b3) freeze drying particles after the first heated to 500-500° C. for 1.5-hours thermal decomposition, then continue to heat up to 850-1100° C. decomposition 2.5-3 hours.
b4) the mixed materials after thermal decomposition are ground into regular particles of 30-50 chevrons in size, and then further ground into nanoparticles with a particle size of 0.2-0.8 nm. In other words, mineral powder rich in nano-calcium is obtained.

Step c) Mixed Granulation and Formed Acid-Relief Agent
Take the natural plant extracts and add deep sea water by the weight ratio 1:(90~120) diluted, then add the mixture with 75~85% of mineral powder, stirring evenly mixed by grout mix, then pour the liquid into the granulator granulation, then get granular relief agent-finished products.

From the above technical solution, in step a), the content of sodium ions in the natural plant extracts are 37,000-66000 mg/kg, and the content of potassium ions are 13750-31300 mg/kg.

The above technical solution, in the step a), described the natural plant extracts in the calcium content is 430-550 mg/kg, iron ion content is 80-110 mg/kg, magnesium ions content is 120-150 mg/kg. the chemical characteristics of natural plant extracts is: in the proportion of 27° C. is 1.230~1.245, the viscosity of 2.875~2.930, pH 12.8~14, the boiling point is 102~104 degrees.

From the above technical solution, the steps in the b1), high-pressure sandblasting is using only 8-12% of the water for the total amount of natural sands or pieces of granite used, the nozzle in the stress of 75-85 psi, the flow rate of 1.0-1.5 gallons per minute for raw material under the condition of injection, injection time for 5-10 min.

From the above technical solution, the steps in the b2), freeze drying temperature is 25~30° C.

The invention also provides a sodium potassium ion and nanometer calcium retardant which is prepared by the preparation method mentioned above.

Beneficial effect of the present invention: the preparation method of a sodium potassium ion and nanometer calcium sustained-release agent is used after stacking fermentation to join a variety of plants are rich in a variety of trace elements and minerals deep sea water has been added to the plant extracts, and foods high in calcium, shellfish and mica ore after grinding, thermal decomposition and other special craft processing system into nanometer level calcium powder, plant extracts after dilution with calcium powder and mixing granulation relief agent-finished products. When used, put the relief agent in a pot of water, it will dilute gradually in the water and can be directly sprayed on the surface of the fruit or soak the fruit in it. It will remove the harmful pesticides, antibiotics, and hormone and other acidic compounds and heavy metals.

Compared with the Existing Technology, the Invention has the Following Advantages:

(1) the nano-grade calcium rich in mineral powder in the raw materials of the present invention can react with various acid compounds; Plant extracts can provide high alkaline environment, and can completely soluble in water, its rich in sodium, potassium ions to form sodium potassium mercury will add speed contact material of chemical reaction, catalytic combined characteristics, strong penetration, is advantageous to the elements and compounds reduction into need to absorb, coupled with nano-sized calcium mutual coordination, through the role of the sustained-release particles after soluble in water, which can thoroughly remove enough ingredients and ingredient within the surface of the harmful pesticides, pesticides, antibiotics and growth hormones and other acidic compounds and heavy metals;

(2) the invention adopts a special process in the preparation of mineral powder, with the method of high pressure water blasting cleaning material surface can be quickly removed attached to the surface layer and the pollution of heavy metals, and then made into nanoscale particles through thermal decomposition and grinding technology, it is easier to be absorbed, make acid neutralization reaction more thoroughly, but also avoid the secondary pollution;

(3) the raw material of the present invention is also rich in a variety of trace elements and minerals, raw materials are purely natural, rich source, as this is low, and the preparation technology is simple, convenient operation, stable quality, high yield, can be large-scale industrial production. Specific implementation mode. The invention is further described in combination with the following examples.

Example 1 in this example, a method for preparing a sodium potassium ion and nanometer calcium sustainer are the following steps:

Step a) Preparation of Natural Plant Extracts Rich in Sodium Potassium Ions a1) banana leaves in 80 weight portion, potato skins in 80 weight portion, and sweet potato rhizome in 60 weigh portion. Emperor bean rhizome, grape leaves, fig rhizome, tendrils leave and seaweeds in total of 50 weight portion. By volume percentage, add concentration of 120~200 cfu/ml of *lactobacillus* bacteria *streptococcus* liquid 0.04%, lactic acid bacteria 0.03%, acetic acid *bacillus* bacteria liquid 0.03% and *Kluyveromyces marxianus* 0.04%, after blending, stacking fermentation under 42° C. for 20 days, the fermentation plant mixture is done;

a2) Mix the fermented plant mixture and the deep seawater together by the weight ratio of 1:9, then heating the mixture twice according to and combined with the filtrate to obtain the natural plant extract rich in sodium and potassium ions.

The chemical characteristics of natural plant extracts in 27° C., the proportion is 1.235, 2.883 viscosity, pH 13.1, the boiling point is 103 degrees, among them: sodium ion content is 42000 mg/kg, the content of potassium ion is 13750 mg/kg, calcium content is 462 mg/kg, iron ion content is 86 mg/kg, magnesium ions content is 120 mg/kg Step b) Prepare Mineral Powder Rich in Nanometer Calcium b1) Put 38 portion of mica ore, 10 portion of mother-of-pearl, 12 portion of oyster shells, 26 portion of oyster bay mix together with the method of high pressure sand cleaning remove dirt on the surface of the raw material;

High-pressure sand blasting is using 11% of the water of total amount of natural sand or pieces of granite, blend of natural sand or crushed. The nozzle in the pressure of 75-psi, velocity of 1.0 gallons per minute for raw material under the condition of injection, injection time for 10 min;

b2) will be mixed after cleaning material grinding particles made of 250 microns, and then at 25° C. for freeze drying;

b3) Heat freeze drying particles by using 500° C. for 2 hours thermal decomposition, and then continue to heat up to 850° C. thermal decomposition of 3 hours;

b4) the mixed materials after thermal decomposition are first ground into a regular particle of 30 entropy m, and then further ground into a nanometer particle with a particle size of 0.2 nm. In other words, mineral powder rich in nanometer calcium is obtained.

Example 2

In this technical solution, a method for preparing a sodium potassium ion and nano calcium sustainer comprises the following steps:

Step a) Preparation of Natural Plant Extracts Rich in Sodium Potassium Ions a1) Mix banana leaves in 80 weight portion and sweet potato rhizome in 60 weight portion. Emperor bean rhizome in 50 weight portion together. Then proportionally add 120~200 cfu/ml of *lactobacillus* bacteria *streptococcus* liquid 0.03%, lactic acid bacteria 0.01%, 0.01%, acetic acid *bacillus* and *Kluyveromyces marxianus* 0.02%, after blending, stacking fermentation under 37° C. for 25 days, after fermentation the plant mixture are formed.

a2) based on the weight proportion mix the fermented plant mixture and the deep sea water with the ratio of 1:8, then extracted twice by heating and combined with the filtrate to obtain the natural plant extract rich in sodium and potassium ions. The chemical characteristics of natural plant extracts is: in the 27° C., proportion is 1.241, viscosity 2.914, pH 13.5, the boiling point is 103 degrees, among them: sodium ion content is 37000 mg/kg, the content of potassium ion is 21360 mg/kg, calcium content is 520 mg/kg, iron ion content is 92 mg/kg, magnesium ions content is 131 mg/kg.

Step b) Prepare Mineral Powder Rich in Nanometer Calcium b1) Put 30 portion of mica ore, 8 portion of mother-of-pearl, 5 portion of oyster shells, 22 portion of oyster bay mix together with the method of high pressure sand cleaning remove dirt on the surface of the raw material;

use high pressure sand blasting by using 10% of the water based on the total amount of the use of natural sand or pieces of granite, the nozzle in the pressure of 85 psi, the velocity of 1.5 gallons per minute to injection of raw material for 5 minutes.

b2) will be mixed after cleaning material grinding particles made of 300 microns, and then in freeze drying −30° C.;

b3) Heat freeze drying particles by 530° C. for thermal decomposition of 1.8 hours, then continue to heat up to 950° C. thermal decomposition of 2.8 hours;

b4) after thermal decomposition, the mixture was first ground into a regular granule of 40 centile m, and then further ground into a nanometer granule with a particle size of 0.5 nm. In other words, mineral powder rich in nanometer, calcium was obtained.

Step c) Mixed Granulation and Formed Acid-Relief Agent

Take the natural plant extracts and add deep sea water by the weight ratio 1:100 diluted, then add the mixture with 80% of mineral powder, stirring evenly mixed by grout mix, then pour the liquid into the granulator granulation, then get granular relief agent—finished products.

Example 3

In this technical solution, a method for preparing a sodium potassium ion and nanometer calcium sustainer consists of the following steps:

Step a) Prepare Natural Plant Extracts Rich in Sodium and Potassium Ions a1) Put together 80 banana leaves, 80 potato skins, 60 sweet potato rhizome, 30 seaweed, 50 grape leaves, 60 emperor bean rhizome, 50 tendrils leaves. The percentage by proportion, to mix in concentration of 120~200 cfu/ml of *lactobacillus* bacteria *streptococcus* liquid 0.06%, actic acid bacteria 0.04%, acetic acid *bacillus* bacteria liquid 0.01% and *Kluyveromyces marxianus* 0.03%, after blending, accumulate fermentation product under 30° C. for 30 days, fermentation plant mixture is formed;

The plant mixture comprises more than two mixtures in banana leaf, sweet potato rhizome, potato skin, seaweeds, grape leaf, emperor bean rhizome, tendrils leaves. fig rhizome;

a2) Mix fermented plant mixture and the deep seawater at ratio of 1:10, then heated three times, and the filtrate was combined to obtain the natural plant extracts rich in sodium and potassium ions.

The chemical characteristics of natural plant extracts is: in 27° C., the proportion is 1.230, 2.876 viscosity, pH 12.8, the boiling point is 102 degrees, among them: sodium ion content is 53500 mg/kg, the content of potassium ion is 31300 mg/kg calcium content is 550 mg/kg, iron ion content is 102 mg/kg, magnesium ions content is 139 mg/kg Step b) Prepare Mineral Powder Rich in Nanometer Calcium b1) Put 45 portion of mica ore, 15 portion of mother-of-pearl, 13 portion of oyster shells and 24 portion of oyster bay together, mixing together with the method of high pressure sand cleaning remove dirt on the surface of the raw material; High-pressure sandblasting is using 8% of the water of the total amount of natural sand or pieces of granite, blend of natural sand or crushed stone, the nozzle in the pressure of 78 psi, the velocity of 1.2 gallons per minute to injection of raw material for 8 minutes.

b2) will be mixed after cleaning material, grinding particles made of 350 microns, and then on to 28° C. for freeze drying;

b3) freeze drying particles after the first heated to 600° C. for thermal decomposition of 1.5 hours, then continue to heat up to 1100° C. thermal decomposition of 2.5 hours;

b4) the mixed materials after thermal decomposition are first ground into a regular particle of 50 centile m, and then further ground into a nanoparticle with a particle size of 0.8 nm. In other words, mineral powder rich in nanometer calcium is obtained.

Step c) Mixed Granulation and Formed Acid-Relief Agent

Take the natural plant extracts and add deep sea water by the weight ratio 1:100 diluted, then add the mixture with 85% of mineral powder, stirring evenly mixed by grout mix, then pour the liquid into the granulator granulation, then get granular relief agent-finished products.

Example 4

In this technical solution, a method for preparing a sodium potassium ion and nanometer calcium are the following steps:

Step a) Prepare Natural Plant Extracts Rich in Sodium and Potassium Ions a1) 80 portion of banana leaf, 40 portion of sea weed, 50 portion of grape leaves and 60 portion of emperor bean leaves, join separately according to the volume percent concentration of 120~200 cfu/ml of *lactobacillus* bacteria *streptococcus* liquid 0.02%, lactic acid bacteria 0.05%, acetic acid *bacillus* bacteria liquid 0.05% and *Kluyveromyces marxianus* 0.06%, after blending, stacking fermentation under 50° C., 15 days after fermentation of plant mixture is formed.

The plant mixture comprises more than two mixtures in banana leaf, sweet potato rhizome, potato skin, seaweed, grape branch and leaf, emperor bean rhizome and fig rhizome;

a2) Mix the fermented plant mixture and the deep seawater together by the weight ratio of 1:8.5, then heating the mixture three times according to and combined with the filtrate to obtain the natural plant extract rich in sodium and potassium ions.

The chemical characteristics of natural plant extracts in 27° C., the proportion is 1.245, 2.930 viscosity, pH 14, the boiling point is 104 degrees, among them: sodium ion content is 66000 mg/kg, the content of potassium ion is 26180 mg/kg, calcium content is 430 mg/kg, iron ion content is 108 mg/kg, magnesium ions content is 150 mg/kg.

Step b) Prepare Mineral Powder Rich in Nanometer Calcium b1) Put 50 portion of mica ore, 12 portion of mother-of-pearl, 10 portion of oyster shells, and 28 portion of oyster bay together. By using the way of high pressure blast cleaning to remove dirt on the surface of the raw material; High-pressure sand blasting is using 12% of the water of the total amount of the natural sand or pieces of granite, blend of natural sand or crushed stone, the nozzle in the pressure of 82 psi, the velocity of 1.3 gallons per minute to injection of raw material, under the condition of the injection time of 6 minutes;

b2) will be mixed after cleaning material grinding particles made of 320 microns, and then in freeze drying −26° C.;

b3) freeze drying particles after the first heated to 580° C. for thermal decomposition of 1.6 h, then continue to heat up to 1000° C. thermal decomposition of 2.6 hours.

b4) the mixed materials after thermal decomposition are first ground into regular particles with a diameter of 45 centile m, and then further ground into nanoparticles with a particle size of 0.5 nm. In other words, mineral powder rich in nanometer calcium is obtained.

Step c) Mixed Granulation and formed Acid—Relief Agent

Will be described in the natural plant extracts and deep seawater according to weight 1:90 dilution, then add 75% of mineral powder into mixture, stirring evenly mixed by grout mix, slurry into the granulator granulation, get granular relief agent—finished products.

This description is only used to explain the technical solution of the present invention rather than limiting the scope of the invention. Although the invention has been described in detail with reference to the preferred embodiments. Those of ordinary skill in the art will understand the technical solution of the present invention can be modified or equivalently replaced without departing from the essence and scope of the technical solution of the present invention.

The invention claimed is:

1. A method for the preparation of an acid-relief agent rich in potassium, sodium and nanocalcium, comprising the following steps:
   a) preparing a mixture of banana leaves, sweet potato roots, potato skin, seaweed, grape leaves, tendrils leaves, fig roots, emperor bean roots, and deep sea water;
   b) adding suitable bacteria to enable fermentation of said mixture, including *lactobacillus* 0.02-0.06%, lactic *streptococcus* 0.01~0.05%, acetobacteria 0.01-0.04%, Kluyverornyces *marxianus* LAF-4 0.02~0.06%;
   c) blending and fermenting the resulting mixture for 15-30 days at a temperature of 30-50 degrees C.;
   d) adding additional sea water to the resulting fermentation product, in a weight ratio of 1:8 to 1:10;
   e) recovering natural plant extracts from said fermentation product; then
   f) mixing nanocalcium mineral powder and sea water with said extracts, to form the final product.

2. The method of claim 1 wherein said natural plant extracts have a sodium Ion content of 37000-66000 mg/kg, the content of potassium ion is 13750-31300 mg/kg, a calcium content of 430-550 mg/kg, iron ion content of 80-110 mg/kg, and the magnesium ion content is 120-150 mg/kg.

3. The method of claim 2 wherein said natural plant extracts have a viscosity of 2.875-2.930, a pH of 12.8-14, and a boiling point of 102-104 degrees C.

4. The method of claim 1 wherein said nanocalcium mineral powder is obtained from a mixture containing 30-50 parts by weight mica ore, 8-15 parts by wt mother of pearl, 10-15 parts oyster shells and 22-28 parts oyster bay, by first cleaning said mixture with high-pressure sandblasting with natural sand or pieces of granite, blend of natural sand or crush total 8-12% of the amount of water, the nozzle in the stress of 75-75 psi, the flow rate of 1.0-1.5 gallons per minute to spray shot of raw material, under the condition of the injection time for 5-10 min.

* * * * *